US010022171B2

United States Patent
Chaput

(10) Patent No.: US 10,022,171 B2
(45) Date of Patent: Jul. 17, 2018

(54) BONE SCREWS AND BONE SCREW SYSTEMS

(75) Inventor: Christopher Chaput, Temple, TX (US)

(73) Assignee: Scott & White Healthcare, Temple, TX (US)

(*) Notice: Subject to any disclaimer, the term of this patent is extended or adjusted under 35 U.S.C. 154(b) by 206 days.

(21) Appl. No.: 13/559,243

(22) Filed: Jul. 26, 2012

(65) Prior Publication Data

US 2013/0030474 A1    Jan. 31, 2013

Related U.S. Application Data

(60) Provisional application No. 61/511,902, filed on Jul. 26, 2011.

(51) Int. Cl.
*A61B 17/86* (2006.01)
*A61B 17/70* (2006.01)
*A61B 90/00* (2016.01)

(52) U.S. Cl.
CPC ...... *A61B 17/8625* (2013.01); *A61B 17/7044* (2013.01); *A61B 17/7049* (2013.01); *A61B 17/7071* (2013.01); *A61B 17/7035* (2013.01); *A61B 17/8695* (2013.01); *A61B 2090/036* (2016.02)

(58) Field of Classification Search
CPC ........ A61B 17/7001; A61B 17/7032–17/7058; A61B 17/84; A61B 17/86–17/8695; A61B 2017/8655–17/868; F16B 19/12
USPC .............. 606/264–275, 300–331; 411/19, 20
See application file for complete search history.

(56) References Cited

U.S. PATENT DOCUMENTS

| | | | |
|---|---|---|---|
| 2,008,229 A * | 7/1935 | Sharp | 411/424 |
| 4,646,752 A | 3/1987 | Swann et al. | 128/748 |
| 5,011,354 A * | 4/1991 | Brownlee | F16B 15/00 411/439 |
| 5,196,013 A * | 3/1993 | Harms et al. | 606/252 |
| 5,304,179 A * | 4/1994 | Wagner | 606/267 |
| 5,336,225 A * | 8/1994 | Zang | 606/304 |
| 5,474,551 A * | 12/1995 | Finn et al. | 606/264 |
| 5,569,248 A * | 10/1996 | Mathews | 606/264 |
| 6,159,210 A | 12/2000 | Voor | 606/56 |
| 6,280,443 B1 * | 8/2001 | Gu et al. | 606/264 |
| 6,312,259 B1 | 11/2001 | Kvarnstrom et al. | 433/173 |
| 7,186,255 B2 | 3/2007 | Baynham et al. | 606/61 |
| 7,585,299 B2 * | 9/2009 | Rezach | 606/60 |
| 7,643,867 B2 | 1/2010 | Solar et al. | 600/426 |
| 7,892,257 B2 | 2/2011 | Abdelgany | 606/246 |
| 2004/0127909 A1 * | 7/2004 | Morgan | A61B 17/8625 606/308 |

(Continued)

FOREIGN PATENT DOCUMENTS

WO    WO 2010/123859    10/2010

OTHER PUBLICATIONS

Custom Spine, Inc., *Polyaxial Screw System*, ISSYS™ LP Inverted Screw System, Product No. 000400 Rev. B.

*Primary Examiner* — Kevin T Truong
*Assistant Examiner* — Amy Sipp
(74) *Attorney, Agent, or Firm* — Norton Rose Fulbright US LLP

(57) ABSTRACT

Bone screws, such as polyaxial bone screws, with dilations located between the screw head and the threaded portion of the screw, for use in preserving polyaxial functionality of the screw head and/or to which crosslinks may be coupled.

16 Claims, 6 Drawing Sheets

(56) References Cited

U.S. PATENT DOCUMENTS

| | | | |
|---|---|---|---|
| 2005/0059972 A1* | 3/2005 | Biscup | A61B 17/686 606/308 |
| 2005/0131404 A1* | 6/2005 | Mazda | A61B 17/7041 606/264 |
| 2005/0228387 A1* | 10/2005 | Paul | 606/72 |
| 2005/0234457 A1 | 10/2005 | James et al. | 606/69 |
| 2006/0025770 A1* | 2/2006 | Schlapfer | A61B 17/7007 606/328 |
| 2006/0036252 A1 | 2/2006 | Baynham et al. | 606/73 |
| 2006/0184170 A1* | 8/2006 | Kapitan | A61B 17/7007 606/287 |
| 2006/0241594 A1 | 10/2006 | McCarthy et al. | 606/61 |
| 2007/0055244 A1* | 3/2007 | Jackson | A61B 17/7028 606/86 A |
| 2007/0118123 A1 | 5/2007 | Strausbaugh et al. | 606/61 |
| 2008/0056844 A1 | 3/2008 | Aukzemas et al. | 411/353 |
| 2008/0097448 A1 | 4/2008 | Binder et al. | 606/74 |
| 2010/0069960 A1 | 3/2010 | Chaput | 606/249 |
| 2010/0256638 A1 | 10/2010 | Tyber et al. | 606/62 |
| 2011/0190821 A1* | 8/2011 | Chin | A61B 17/7005 606/264 |
| 2014/0046384 A1* | 2/2014 | Horwitz | A61B 17/8883 606/304 |

\* cited by examiner

… (1) …

BONE SCREWS AND BONE SCREW SYSTEMS

CROSS-REFERENCE(S) TO RELATED APPLICATION(S)

This application claims priority to U.S. Provisional Patent Application Ser. No. 61/511,902, filed Jul. 26, 2011, the entire contents of which are expressly incorporated by reference.

BACKGROUND

I. Field of the Invention

This invention relates generally to bone screws and more particularly, in some respects, to bone screws comprising a dilation between the head and the threaded portion that may be configured to be coupled to a crosslink.

II. Description of Related Art

Bone screws are used in numerous surgical operations. In particular, polyaxial bone screws are often used in spinal surgery. Known polyaxial bone screws have a spherical, semi-spherical, or otherwise rounded head, and a cap known sometimes as the "tulip," with the cap and head cooperating to form what is sometimes referred to as the "polyaxial head." A set screw is used to lock a structure such as a rod to the polyaxial head by being threadably engaged with the tulip. The cap may include a socket portion capable of receiving the bone screw at multiple orientations, much like a ball-and-socket joint. This allows some flexibility for the surgeon placing the screws because the orientation of the screw does not typically limit the orientation of the member attached to it.

However, in certain instances, the bone screw is screwed in such that the rounded head becomes incapable of being polyaxially coupled to the cap. For example, the bone screw may be screwed in too far and at such an angle that the cap is not free to move polyaxially with respect to the head of the screw once the head impinges on the surface of the bone. When this happens, the bone screw should not be used to bring two boney surfaces together. The phrase "lag effect" is commonly used to describe what happens when two fractured bones or the surfaces of two joints are compressed by the force of the screw threads in the more distal bone pulling the head of a single screw against the proximal bone; a bone screw in that position is commonly described as a "lag screw." Traditional lag screws have conical heads that lack any intrinsic polyaxial ability and therefore are difficult to incorporate into a construct that involves multiple screws at varying angles. In contrast, screws with polyaxial heads can more easily be incorporated in long constructs with multiple screws of varying angles, as seen in the spine. However, such polyaxial screws are only able to provide compression by placing two separate screws (one in each bone or joint surface), connecting them with a rod, and then applying the compression through the rod.

Multiscrew constructs, in the spine for instance, often incorporate linkages between the screws placed on the right and left sides of the spine to increase stability. Such a "crosslink" is usually done between two screws from rod to rod, or it can be done from the top of one polyaxial head to another. Placing the crosslink on the rods can sometimes be difficult or impossible because there is often little space between the screw heads on the rod to place the crosslink. When the crosslink is attached to the top of a polyaxial screw, sometimes the angulation of the two screws is very different and it is difficult or impossible to attached a rigid crosslink that matches those angles.

SUMMARY

Some embodiments of the present bone screws are configured to allow the cap to rotate about both the axis of the screw and about at least one other axis that is positioned at a non-zero angle with respect to the axis of the screw when the screw is used to couple a rod to a bone. Some embodiments of the present bone screws are configured with a dilation to which a crosslink can be polyaxially coupled when the screw is implanted into bone, and where the cap can rotate about both the axis of the screw and about at least one other axis that is positioned at a non-zero angle with respect to the axis of the screw when the screw is used to couple a rod to a bone.

Some embodiments of the present bone screws comprise a shaft having an axis about which the shaft can rotate, and a shaft dimension along a line substantially perpendicular to and intersecting the axis, the shaft comprising a threaded portion that has a top; a head fixed to the shaft and configured to be coupled to a cap, the head having a bottom; and a dilation coupled to or integral with the shaft, the dilation having a dilation dimension along a line substantially perpendicular to and intersecting the axis and spaced apart from both the bottom of the head and from the top of the threaded portion, the dilation dimension being greater than the shaft dimension. The dilation may be fixed to the shaft such that the two cannot move relative to each other. Some further embodiments also comprise a cap configured to be coupled to the head of the bone screw.

Some embodiments of the present bone anchoring systems comprise a bone screw that includes a shaft having an axis about which the shaft can rotate, and a shaft dimension along a line substantially perpendicular to and intersecting the axis, the shaft comprising a threaded portion that has a top; a head fixed to the shaft and configured to be coupled to a cap, the head having a bottom; a dilation coupled to or integral with the shaft, the dilation having a dilation dimension along a line substantially perpendicular to and intersecting the axis and spaced apart from both the bottom of the head and from the top of the threaded portion, the dilation dimension being greater than the shaft dimension; and a cap configured to be coupled to the head of the bone screw. The dilation may be fixed to the shaft such that the two cannot move relative to each other.

Some embodiments of the present bone anchoring systems comprise first and second bone screws, each bone screw comprising a shaft having an axis about which the shaft can rotate, and a shaft dimension along a line substantially perpendicular to and intersecting the axis, the shaft comprising a threaded portion that has a top; a head fixed to the shaft and configured to be coupled to a cap, the head having a bottom; and a dilation coupled to or integral with the shaft, the dilation having a dilation dimension along a line substantially perpendicular to and intersecting the axis and spaced apart from both the bottom of the head and from the top of the threaded portion, the dilation dimension being greater than the shaft dimension. The system may also include a crosslink, where the dilation of the first bone screw and the crosslink are configured to be polyaxially coupled to each other and the dilation of the second bone screw and the crosslink are configured to be polyaxially coupled to each other. Each dilation may be fixed to the shaft of its respective bone screw, such that the two cannot move relative to each other.

The term "coupled" is defined as connected, although not necessarily directly, and not necessarily mechanically.

The terms "a" and "an" are defined as one or more unless this disclosure explicitly requires otherwise.

The term "substantially" and its variations (e.g. "approximately" and "about") are defined as being largely but not necessarily wholly what is specified (and include wholly what is specified) as understood by one of ordinary skill in the art. In any embodiment of the present disclosure, the terms "substantially," "approximately," and "about" may be substituted with "within [a percentage] of" what is specified, where the percentage includes 0.1, 1, 5, 10, and 15 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed. Metric units may be derived from the English units provided by applying a conversion and rounding to the nearest millimeter.

The feature or features of one embodiment may be applied to other embodiments, even though not described or illustrated, unless expressly prohibited by this disclosure or the nature of the embodiments.

Any embodiment of any of the present devices and methods can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Other features and associated advantages will become apparent with reference to the following detailed description of specific embodiments in connection with the accompanying drawings.

BRIEF DESCRIPTION OF THE DRAWINGS

The following drawings illustrate by way of example and not limitation. For the sake of brevity and clarity, every feature of a given structure may not always be labeled in every figure in which that structure appears. Identical reference numbers do not necessarily indicate an identical structure. Rather, the same reference number may be used to indicate a similar feature or a feature with similar functionality, as may non-identical reference numbers.

DETAILED DESCRIPTION

Various features and advantageous details are explained more fully with reference to the nonlimiting embodiments that are illustrated in the accompanying drawings and detailed in the following description. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those of ordinary skill in the art from this disclosure.

In the following description, numerous specific details are provided to provide a thorough understanding of the present embodiments. One of ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
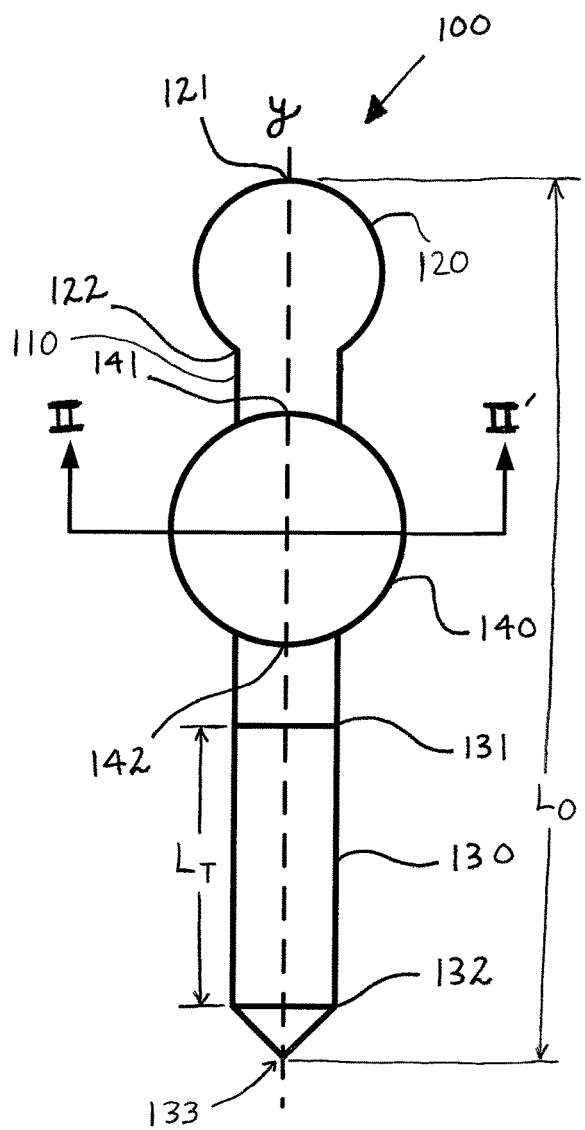
FIG. 1 is a side view of an embodiment of one of the present bone screws.

FIG. 1 illustrates a side view of bone screw 100, one embodiment of the present bone screws. Bone screw 100 comprises a shaft 110 having an axis y about which bone screw 100 can rotate. Bone screw 100 comprises a head 120 that is fixed to shaft 110 (integrally, in the depicted embodiment, but could be a different piece that is coupled to the shaft in other embodiments) and that has a head top 121 and a head bottom 122. Head 120 is fixed to shaft 110 such that the two cannot move with respect to each other, including before a cap (see FIG. 3) is coupled to head 120. Bone screw 100 also comprises a threaded portion 130 having a threaded portion top 131 and a threaded portion bottom 132. Threaded portion bottom 132 may terminate at bottom 133 of the screw, which may be in a sharp point. In other embodiments, the threaded portion may terminate above bottom 133 of the screw, and the bottom of the screw (regardless of where the threaded portion ends) may have any suitable shape, such as rounded or flat.

Bone screw 100 has an overall length $L_O$, which is the distance between head top 121 and screw bottom 133. Bone screw 100 also has a threaded portion length $L_T$, which is the distance between threaded portion top 131 and threaded portion bottom 132. In some embodiments, $L_T$ may be equal to the distance between threaded portion top 131 and screw bottom 133 because threaded portion bottom 132 may coincide with screw bottom 133. Overall length $L_O$ may be between about 10 millimeters (mm) and about 80 mm. In certain embodiments (e.g., where bone screw 100 is a cervical screw), $L_O$ may be less than about 10 mm, 12 mm, 14 mm, 16 mm, 18 mm, 20 mm, 22 mm, or 24 mm. In other embodiments (e.g., where bone screw 100 is a thoracic screw), $L_O$ may be less than about 25 mm, 30 mm, 35 mm, 40 mm, 45 mm, 50 mm, or 55 mm. In still other embodiments, (e.g., where bone screw 100 is a lumbar screw), $L_O$ may be less than about 30 mm, 35 mm, 40 mm, 45 mm, 50 mm, 55 mm, 60 mm, 65 mm, 70 mm, 75 mm, or 80 mm.

Threaded portion length $L_T$ may be between about 8 mm and 55 mm.

Bone screw 100 further comprises a dilation 140. In some embodiments, dilation 140 may be coupled to shaft 110. In other embodiments, dilation 140 is integral with shaft 110. Dilation 140, whether coupled to or integral with shaft 110, may be fixed to shaft 110 such that the two cannot move with respect to each other. Dilation 140 is located on shaft 110 between head bottom 122 and threaded portion top 131. Dilation 140 comprises a dilation top 141 spaced apart from head bottom 122 and a dilation bottom 142 spaced apart from threaded portion top 131.

Plane II-II' is substantially perpendicular to axis y and intersects bone screw 100 through dilation 140. Dilation 140 has a dilation dimension $D_D$ along a line substantially perpendicular to and intersecting axis y, which line may be positioned in plane II-II'. Shaft 110 has a shaft dimension $D_S$ that is the distance of the longest straight line that intersects in two places the shape formed by the intersection of shaft 110 and a plane between dilation top 141 and head bottom 122 or between dilation bottom and threaded portion top 131 that is parallel to plane II-II'; such plane is also substantially perpendicular to and intersects axis y. Dilation dimension $D_D$ will be a diameter where dilation 140 is spherical, and shaft dimension $D_S$ will be a diameter where shaft 110 is a cylinder. Dilation dimension $D_D$ may, but need not, be located midway between dilation top 141 and dilation bottom 142.

In some embodiments, dilation dimension $D_D$ is greater than shaft dimension $D_S$. In certain preferred embodiments, the dilation dimension $D_D$ is 101 to 500 percent of shaft dimension $D_S$, including any integer between 101 and 300 and all ranges between (and including) all such integers. For example, for embodiments of the present bone screws that are configured for use in the cervical spine where $D_S$ is 3 millimeters (mm) (the outer diameter of threaded portion may be 3.5 mm), $D_D$ may be 4-9 mm; preferably, $D_D$ does not exceed the diameter of the cap (see cap 200 in FIG. 3). As another example, for embodiments of the present bone screws that are configured for use in the lumbar spine where $D_S$ is 4 mm, $D_D$ may be 10-16 mm. As another example, for embodiments of the present bone screws that are configured for use in the thoracic spine where $D_S$ is 4 mm, $D_D$ may be 12 mm. In some embodiments, dilation dimension $D_D$ may be substantially the same as a comparable dimension of head 120.

In some embodiments, the bottom portion of dilation 140 may be provided with cutting flutes (not shown) for applications in which the dilation impinges directly on bone.

Figure 2A:
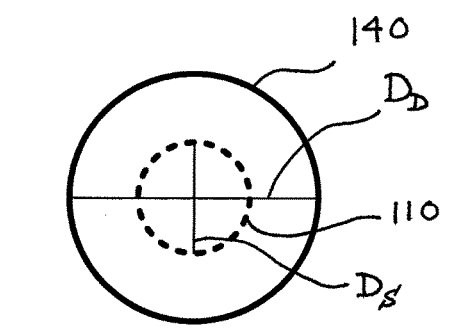
FIGS. 2A-2C are cross-sectional views of embodiments of the present bone screws.
Figure 2B:
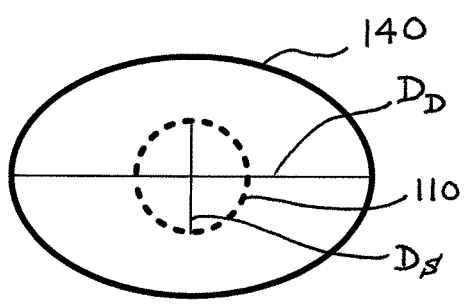
Figure 2C:
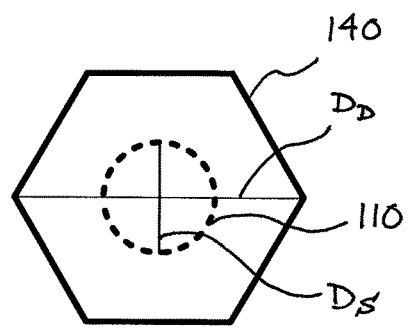

FIGS. 2A-2C illustrate cross-sectional views of embodiments of bone screw 100 having dilations 140 with different shapes. For example, FIG. 2A shows an embodiment of bone screw 100 in which dilation 140 is substantially spherical. In such an embodiment, dilation dimension $D_D$ is any diameter of the circle formed by the substantially perpendicular intersection of a plane (e.g., plane II-II') passing through dilation 140 and axis y.

Further, FIG. 2B shows an embodiment of bone screw 100 in which dilation 140 is substantially ellipsoidal (i.e., a three-dimensional ellipse). In such an embodiment, dilation dimension $D_D$ is a distance taken along a straight line between two points of intersection with dilation 140 provided that line substantially intersects axis y and lies in a plane that is, or is parallel to, plane II-II'.

In addition, FIG. 2C shows an embodiment of bone screw 100 in which dilation 140 is substantially a regular hexagonal prism (i.e., a regular hexagon extruded along axis y). In such an embodiment, dilation dimension $D_D$ is a distance taken along a straight line between two points of intersection with dilation 140 provided that line substantially intersects axis y and lies in a plane that is, or is parallel to, plane II-II'. Still other embodiments of bone screw 100 may comprise a dilation 140 having the shape of a cube, pentagonal prism, or octagonal prism.

In various embodiments, shaft dimension $D_S$ is a diameter between about 3.5 mm and about 8 mm. In certain embodiments (e.g., where bone screw 100 is a cervical screw), shaft dimension $D_S$ is a diameter that may be less than about 3.5 mm, 4.0 mm, or 4.5 mm. In other embodiments (e.g., where bone screw 100 is a thoracic screw), shaft dimension $D_S$ is a diameter that may be less than about 4.0 mm, 5.0 mm, 6.0 mm, 6.5 mm, or 7.0 mm. And in still other embodiments (e.g., where bone screw 100 is a lumbar screw) shaft dimension $D_S$ is a diameter that may be less than about 5.0 mm, 6.0 mm, 7.0 mm, or 8.0 mm.

In certain embodiments, dilation dimension $D_D$ taken midway between dilation top 141 and dilation bottom 142 is 4 to 16 mm, including every integer in between and all ranges between (and including) all such integers.

Figures 2D, 2E:
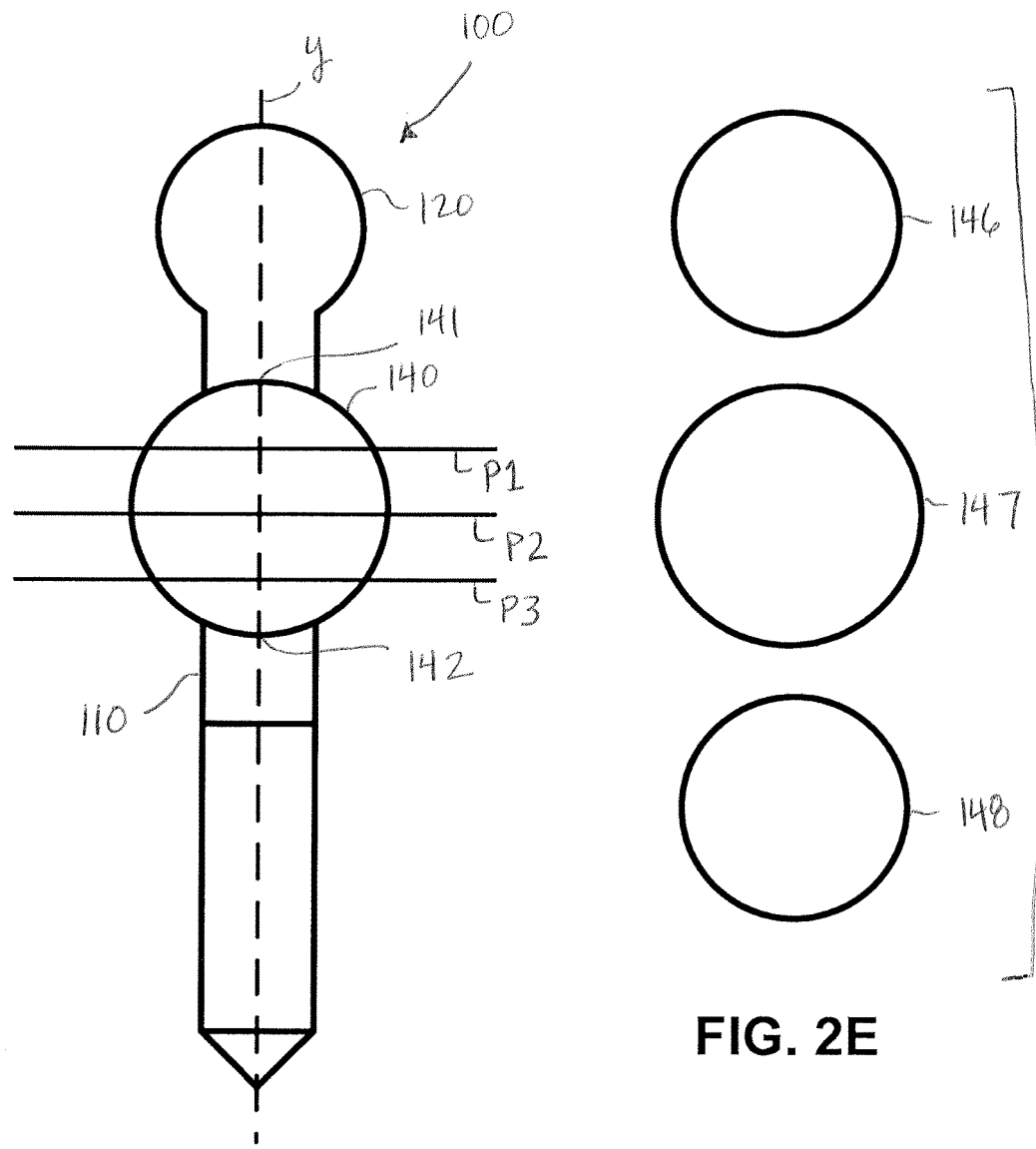
FIG. 2D is a side view of the bone screw shown in FIG. 1, depicting different planes in which different outer perimeters of the dilation along the axis of the screw shaft are positioned.
FIG. 2E shows the different outer perimeters identified in FIG. 2D.

As illustrated in FIG. 2D, dilation 140 of bone screw 100 may have an outer perimeter that varies along axis 7 from top 141 to bottom 142. FIG. 2D shows different planes P1, P2, and P3 oriented perpendicular to axis y and parallel to each other that intersect the bone screw an in which first outer perimeter 146, second outer perimeter 147, and third outer perimeter 148 (shown in FIG. 2E) are positioned. As FIG. 2E shows, second outer perimeter 147 is greater than first outer perimeter 146 and it is greater than third outer perimeter 148. In embodiments of the present bone screws in which the dilation has an irregularly shaped surface (not shown), the respective exemplary outer perimeters will be irregularly shaped and can be compared by comparing the areas they each define, such that the second area defined the second outer perimeter can be greater than the area defined by the first outer perimeter and it is greater than the area defined by the third outer perimeter.

Figure 3:
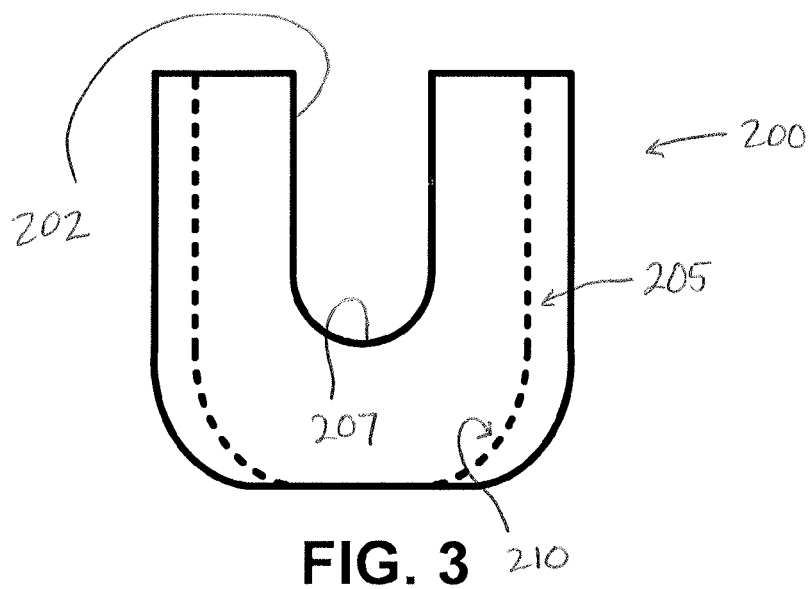
FIG. 3 is a side view of a generic representation of a cap configured to be coupled to a bone screw.

FIG. 3 is a side view of an embodiment of a cap 200, which is configured to be coupled to bone screw 100 and, more particular, to head 120 of bone screw 100. Various embodiments of cap 200 comprise a socket portion 210 located at the lower end of inner wall 205. Cap 200, and more specifically socket portion 210, and head 120 are configured to be coupled to each other. Such coupling may be achieved using, for example, a threaded insert, as described below, or in any other suitable manner understood to those of ordinary skill in the art. In certain embodiments, cap 200, and more specifically socket portion 210, and head 120 are configured to be polyaxially coupled to each other such that socket portion 210 may receive head 120 at one of a number of orientations. In this regard, the cap and head of embodiments of the present bone screws are preferably configured such that the cap may tilt back and forth at several (up to an infinite number) of discrete positions separated from each other by some amount of rotation of the cap about axis y of the screw. In general, this may be accomplished at least in part by making the bottom opening of the cap larger than diameter of the shaft portion that is immediately below the head. In other embodiments, socket portion 210 may be threaded and the socket portion and the head may be coupled in manner that does not allow for movement between the head and the socket in multiple directions. In certain embodiments, cap 200 comprises one or more channels 202 (e.g., two channels 202), which may be located on opposing sides of cap 200 and which, in the embodiment shown, include a curved bottom 207 against which a rod or other structure may rest when captured between the curved bottom and the bottom of a threaded insert (not shown) that is screwed into cap 200 (as one of ordinary skill in the art will understand from this disclosure); in such embodiments, a top portion of inner wall 205 of cap 200 may be threaded and configured to mate with such a threaded insert.

Figure 4:
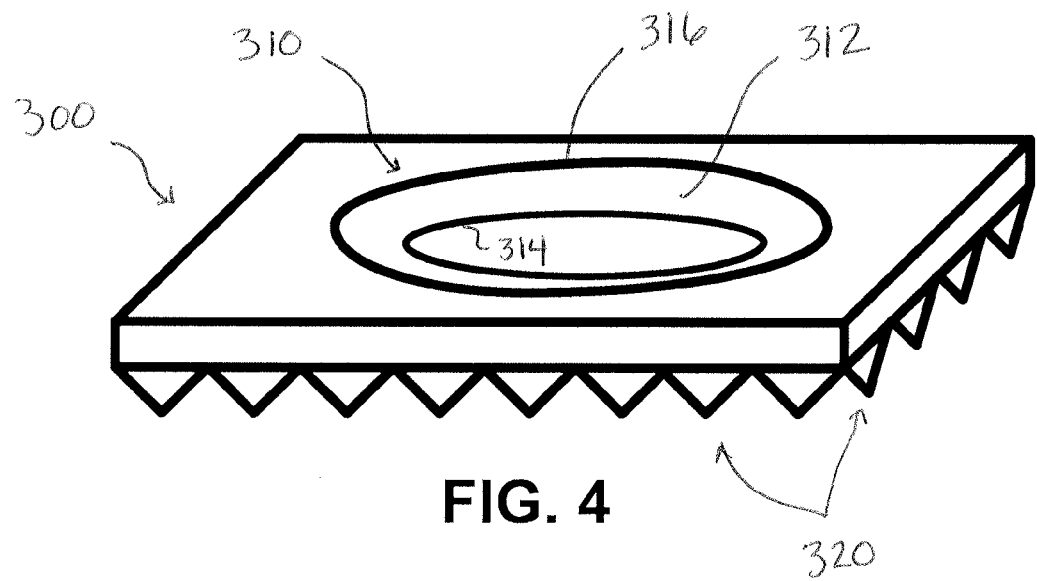
FIG. 4 is a perspective view of an embodiment of one of the present washers configured to be coupled to an embodiment of one of the present bone screws.

In certain embodiments, bone screw 100 may be configured to be coupled to a washer 300 (which may also be referred to as a plate or lag plate). FIG. 4 is a perspective view of one embodiment of such a washer. In the embodiment shown, washer 300 comprises a plurality of cleats 320, which may be configured to increase washer 300's resistance to movement when placed against bone or a similar material. In other embodiments, washer 300 does not comprise cleats. The cleats may be located at any desirable locations along the underside of the washer, such around the perimeter of the washer (and not in the space between the perimeter and the bottom opening of the hole discussed in the next paragraph) or across the entire bottom surface of the washer.

Washer 300 further comprises a hole 310 that is configured to receive shaft 110 of bone screw 100. In certain embodiments, hole 310 has a portion 312 that is tapered to receive a bottom portion of dilation 140 such that washer 300 may more closely mate to bone screw 100. Opening 314 formed by the bottom of hole 310 is smaller than opening 316 formed by the top of hole 310 in such embodiments.

Figure 5:
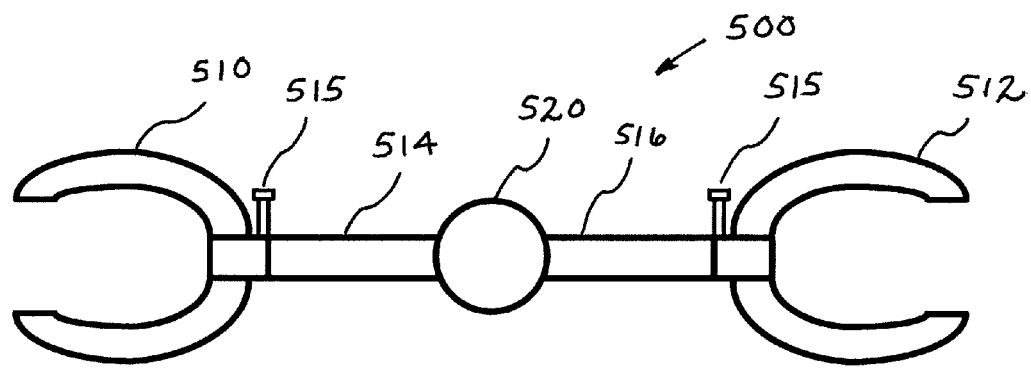
FIG. 5 is a top view of an embodiment of one of the present crosslinks comprising two clamps.
Figure 6:
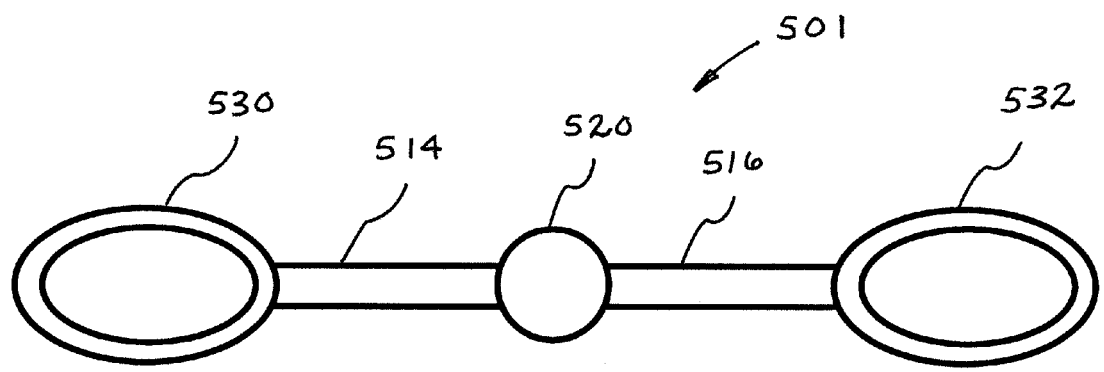
FIG. 6 is a top view of an embodiment of one of the present crosslink comprising two bands.

Embodiments of bone screw 100 and embodiments of one of the present crosslinks are shown in FIGS. 5 and 6. A top view of one embodiment of crosslink 500 is shown in FIG. 5. The illustrated embodiment of crosslink 500 comprises a first link member 514 coupled to a second link member 516 via a joint 520. A first clamp 510 is coupled to first link member 514 and a second clamp 512 is coupled to second link member 516. The clamps are configured to be coupled to some embodiments of the present bone screws; more particularly, the clamps are configured to be coupled to the dilations (respectively) of some embodiments of the present bone screws, and may be adjusted to achieve the coupled relationships using clamp adjusters 515. Crosslink 500 may be any suitable commercially-available crosslink.

In other embodiments, one of the present crosslinks may comprise bands configured to be coupled to embodiments of the present dilations. Crosslink 501, a top view of which is shown in FIG. 6, comprises a first band 530 and a second band 532. In some embodiments, bands 530, 532 are substantially elastic or comprise elastic materials. In others, bands 530, 532 are substantially inelastic but the length of bands 530, 532 is configured to be adjusted (e.g., loosened and tightened) by a user, such as through the use of a slipknot (not shown) or a sheath (not shown).

Figure 7:
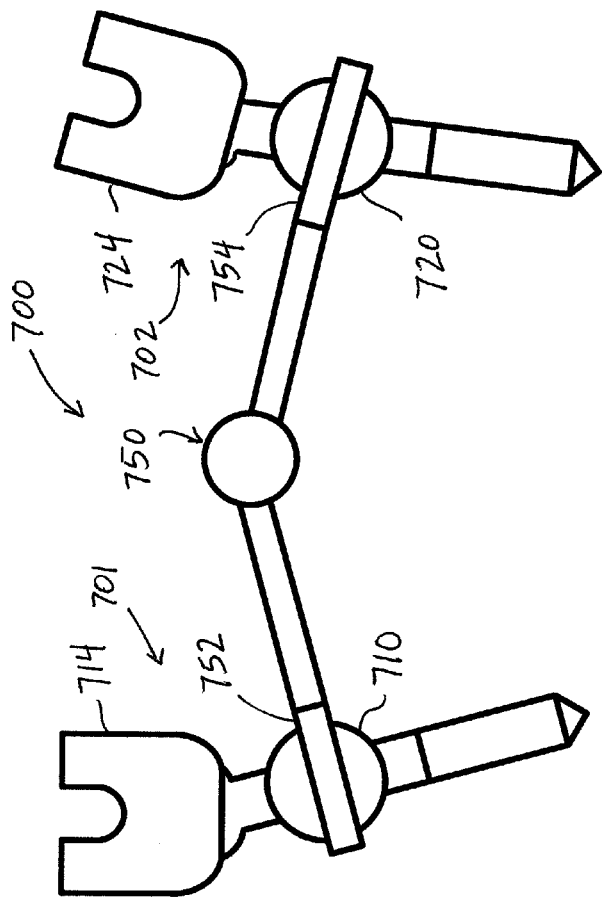
FIG. 7 is a side view of an embodiment of one of the present systems comprising two bone screws and a crosslink.

FIG. 7 illustrates a side view of system 700, an embodiment of one of the present systems in which two bone screws and a crosslink are polyaxially coupled to each other. First bone screw 701 is shown polyaxially coupled to a first cap 714 and second bone screw 702 is shown polyaxially coupled to a second cap 724. Crosslink 750 comprises a first clamp 752 that is polyaxially coupled to dilation 710 of first bone screw 710. Crosslink 750 also comprises a second clamp 752 that is polyaxially coupled to dilation 720 of second bone screw 702. As FIG. 7 shows, embodiments of the present bone screws are configured such that the dilation of the screw does not contact the cap when the cap is coupled to the head.

Figure 8:
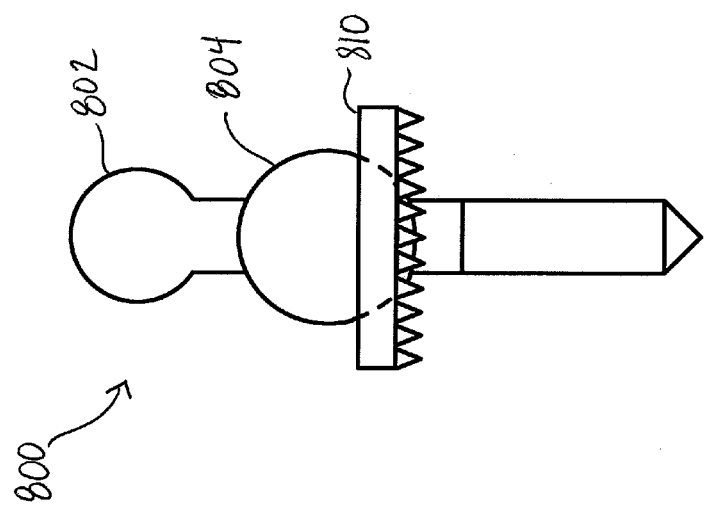
FIG. 8 illustrates a side view of one of the present systems that includes one of the present bone screws in contact with one of the present washers, or lag plates.

FIG. 8 illustrates a side view of one of the present systems that includes one of the present bone screws in contact with one of the present washers. System 800 includes bone screw 802 in contact with washer 810. More particularly, dilation 804 of bone screw 802 is shown in contact with washer 810; when the bone screw is engaged with bone and the cleats of washer 810 are in contact with bone, the washer may be characterized as being polyaxially coupled to the bone screw. Such a configuration may be used, for example, in an application in which it is desirable to keep both the head of the bone screw and the cap that may be coupled to the head out of contact with bone, thus allowing the cap to move in a polyaxial manner relative to the head of the bone screw (or vice-versa). Washer 300 may also be characterized as a plate or a lag plate.

Figure 9:
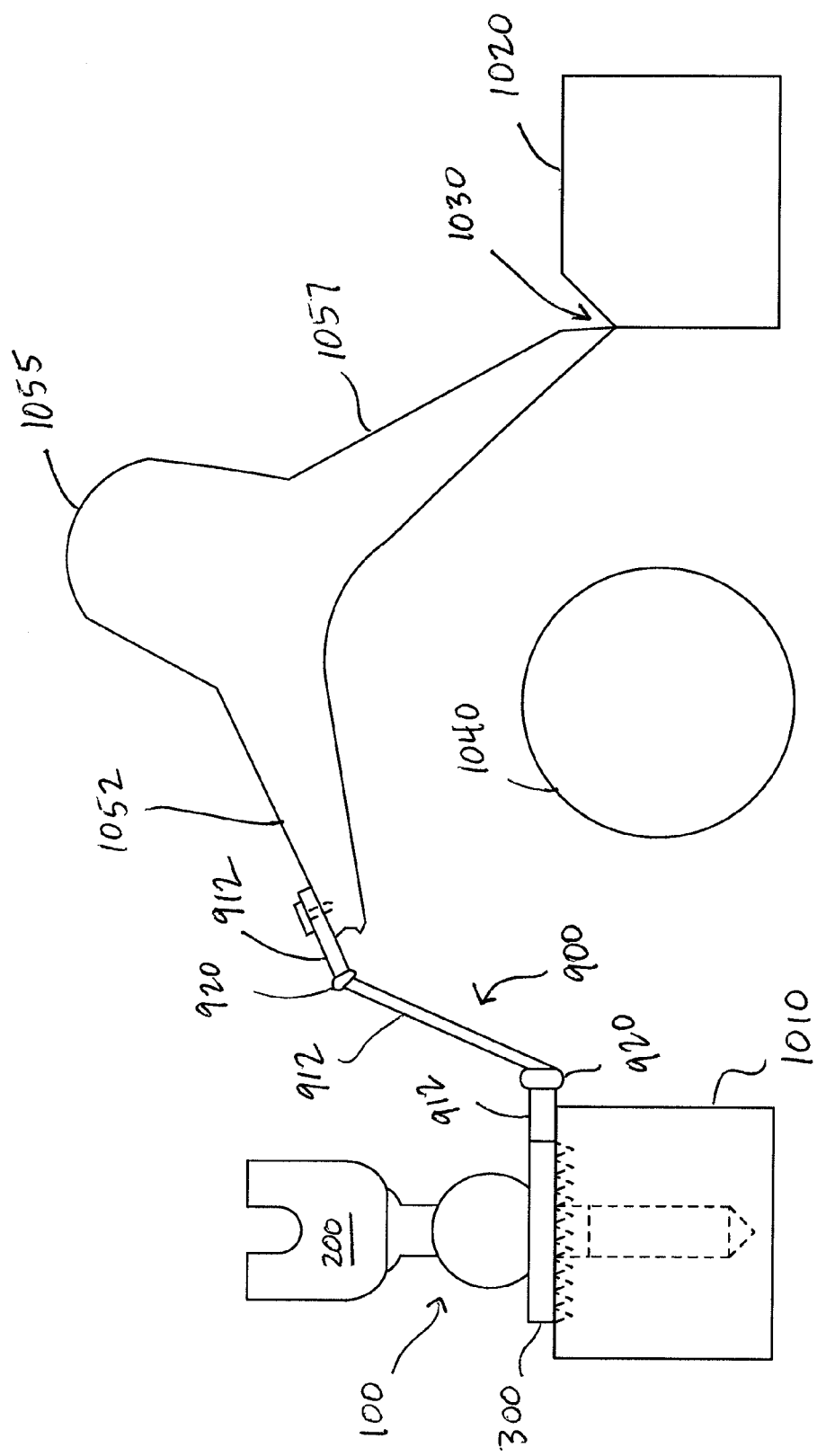
FIG. 9 illustrates one embodiment of the present bone screw anchoring systems used in a laminoplasty setting.

FIG. 9 illustrates use of embodiment of one of the present bone screw anchoring systems used in a laminoplasty setting. This figure shows bone screw 100, which includes cap 200, coupling crosslink 900 via lag plate 300 to which the crosslink is rigidly coupled. Crosslink 900 includes multiple joints 920 movably coupling links (or rod) 912 together. Screw 100 is attached to left lateral mass 1010. Crosslink 900 is attached to left lamina 1052, which is directly connected to spinous process 1055, which is directly connected to right lamina 1057, which is directly connected to a right lateral mass 1020 via groove, or hinge, 1030. Spinal cord 1040 is shown for context.

It should be understood that the present devices and methods are not intended to be limited to the particular forms disclosed. Rather, they are to cover all modifications, equivalents, and alternatives falling within the scope of the claims. For example, in other embodiments of system 700, crosslink 750 comprises bands configured to be polyaxially coupled to the dilations of the bone screws. In still other embodiments of system 700, such as those comprising bone screws with dilations that are regular hexagonal prisms, the bone screws and the crosslink are not configured to be polyaxially coupled to each other and are instead configured to be coupled to each other.

Embodiments of the present dilations may act as a stop against a particular one of the present bone screws from being driven further into bone, thus better ensuring that the bottom of head of the bone screw will be a sufficient distance from the bone such that a cap coupled to the head will retain the polyaxial that would otherwise be lost if the cap abutted the bone or was too close to the bone. Furthermore, embodiments of the present dilations may also act as a polyaxial coupling location for a crosslink. As a result, in some circumstances, greater functionality may be achieved with embodiments of the present bone screws than with some existing bone screws. The present dilations may be made from any suitable material, including any of the materials from which existing bone screw shafts are made such as titanium and various alloys thereof, stainless steel, cobalt chromium, and polyetheretherketone (PEEK).

The claims are not to be interpreted as including means-plus- or step-plus-function limitations, unless such a limitation is explicitly recited in a given claim using the phrase(s) "means for" or "step for," respectively.

The invention claimed is:

1. A bone screw comprising:
   a shaft having an axis about which the shaft can rotate, and a shaft dimension along a line substantially perpendicular to and intersecting the axis, the shaft comprising a threaded portion that has a top;
   a round head fixed to the shaft and configured to be polyaxially coupled to a cap, the head having a bottom and a spherical surface that defines a circular outer perimeter in a plane that is perpendicular to the axis, a diameter of the circular outer perimeter defining a maximum transverse dimension of the head; and
   a dilation coupled to or integral with the shaft, the dilation having:
      an upper half that is convex;
      a dilation dimension along a line substantially perpendicular to and intersecting the axis and spaced apart from both the bottom of the head and the top of the threaded portion, the dilation dimension being greater than the shaft dimension; and
      a profile in a cross-section taken parallel to the axis, the profile being curved from a first location where the dilation meets the shaft to a second location spaced halfway between a top and a bottom of the dilation, the second location being disposed between the first location and the threaded portion.

2. The bone screw of claim 1, further comprising:
   a cap configured to be coupled to the head of the bone screw.

3. The bone screw of claim 1, where the dilation dimension is 250 to 500 percent of the shaft dimension.

4. The bone screw of claim 1, where the dilation has a substantially-circular cross-section in a plane substantially perpendicular to the axis.

5. The bone screw of claim 4, where the dilation has a top, a bottom, a first outer perimeter in a first plane that is perpendicular to the axis and positioned between the top of the dilation and the dilation dimension, a second outer perimeter positioned in a second plane parallel to the first plane and intersecting the dilation dimension, and a third outer perimeter positioned in a third plane parallel to the first plane and positioned between the dilation dimension and the bottom of the dilation, the second outer perimeter being greater than the first outer perimeter and being greater than the third outer perimeter.

6. The bone screw of claim 5, further comprising a cap configured to be coupled to the head of the bone screw, the bone screw being configured such that the dilation does not contact the cap when the cap is coupled to the head.

7. The bone screw of claim 4, where the dilation has a top, a bottom, a first outer perimeter in a first plane that is perpendicular to the axis and positioned between the top of the dilation and the dilation dimension, a second outer perimeter positioned in a second plane parallel to the first plane and intersecting the dilation dimension, and a third outer perimeter positioned in a third plane parallel to the first plane and positioned between the dilation dimension and the bottom of the dilation, the first outer perimeter defining a first area, the second outer perimeter defining a second area, and the third outer perimeter defining a third area, the second area being greater than the first area and being greater than the third area.

8. The bone screw of claim 1, where the dilation has a substantially-elliptical outer perimeter in a plane that is substantially parallel to the axis.

9. The bone screw of claim 1, where the dilation has a substantially-elliptical outer perimeter in a plane that is substantially perpendicular to the axis.

10. The bone screw of claim 1, where the bone screw has an overall length that is between about 10 mm and about 80 mm.

11. The bone screw of claim 10, where the dilation dimension is 4 millimeters to 16 millimeters.

12. A bone anchoring system comprising:
    a bone screw comprising:
       a shaft having an axis about which the shaft can rotate, and a shaft dimension along a line substantially perpendicular to and intersecting the axis, the shaft comprising a threaded portion that has a top;
       a head fixed to the shaft and configured to be coupled to a cap, the head having a bottom and a spherical surface that defines a circular outer perimeter in a plane that is perpendicular to the axis, a diameter of the circular outer perimeter defining a maximum transverse dimension of the head; and
       a dilation coupled to or integral with the shaft, the dilation having:
          a maximum dilation dimension along a line substantially perpendicular to and intersecting the axis and spaced apart from both the bottom of the head and from the top of the threaded portion, the dilation dimension being greater than the shaft dimension; and
          an ellipsoidal surface having a diameter at the dilation dimension, a portion of the ellipsoidal surface extending from the dilation dimension and toward the head.

13. The system of claim 12, where:
    the system comprises a cap configured to be coupled to the head of the bone screw;
    the cap and the head are configured to be polyaxially coupled to each other; and
    the dilation dimension is 250 to 500 percent of the shaft dimension.

14. The bone screw of claim 13, where the bone screw is configured such that the dilation does not contact the cap when the cap is coupled to the head.

15. The bone screw of claim 12, where the dilation has a top, a bottom, a first outer perimeter in a first plane that is perpendicular to the axis and positioned between the top of the dilation and the dilation dimension, a second outer perimeter positioned in a second plane parallel to the first plane and intersecting the dilation dimension, and a third outer perimeter positioned in a third plane parallel to the first plane and positioned between the dilation dimension and the bottom of the dilation, the second outer perimeter being greater than the first outer perimeter and being greater than the third outer perimeter.

16. The bone screw of claim 12, where the dilation has a top, a bottom, a first outer perimeter in a first plane that is perpendicular to the axis and positioned between the top of the dilation and the dilation dimension, a second outer perimeter positioned in a second plane parallel to the first plane and intersecting the dilation dimension, and a third outer perimeter positioned in a third plane parallel to the first plane and positioned between the dilation dimension and the bottom of the dilation, the first outer perimeter defining a first area, the second outer perimeter defining a second area, and the third outer perimeter defining a third area, the second area being greater than the first area and being greater than the third area.

\* \* \* \* \*